United States Patent [19]

Wagner et al.

[11] Patent Number: 4,683,418
[45] Date of Patent: Jul. 28, 1987

[54] MOISTURE MEASURING METHOD AND APPARATUS

[75] Inventors: Edward D. Wagner; Richard R. Trautwein, both of Rogue River, Oreg.

[73] Assignee: Wagner Electronic Products, Inc., Rogue River, Oreg.

[21] Appl. No.: 638,020

[22] Filed: Aug. 6, 1984

[51] Int. Cl.⁴ .......................................... G01R 27/26
[52] U.S. Cl. .................................. 324/61 P; 324/61 R
[58] Field of Search ............... 324/61 R, 61 P, 65 R, 324/437

[56] References Cited

U.S. PATENT DOCUMENTS 3,959,723  5/1976  Wagner .............................. 324/61 P
4,377,783  3/1983  Wagner .............................. 324/61 R

FOREIGN PATENT DOCUMENTS 236230  7/1960  Australia ........................... 324/61 R
218755 12/1961  Austria ............................... 324/61 P
2150928  4/1972  Fed. Rep. of Germany .... 324/61 P

*Primary Examiner*—Reinhard J. Eisenzopf
*Assistant Examiner*—Jose M. Solis
*Attorney, Agent, or Firm*—Dellett, Smith-Hill and Bedell

[57] ABSTRACT

Moisture in wood veneer strips received from a drying oven is measured by passing a first radio frequency signal through the veneer for reception by a receiving plate, transmitting a second radio frequency signal in out-of-phase relation to the first radio frequency signal for reception by the receiving plate, the second signal not passing through the wood. The first and second radio frequency signals induce a potential in the receiving plate, the induction of the first radio frequency signal varying in accordance with the moisture contained in the veneer. The potential of the receiving plate is then measured to determine the extent of moisture in the veneer.

11 Claims, 4 Drawing Figures

MOISTURE MEASURING METHOD AND APPARATUS

BACKGROUND OF THE INVENTION

The present invention relates to a method and an apparatus for measuring moisture in material, and particularly to an improved apparatus which is less sensitive to the positioning or thickness of the material than prior art devices.

Moisture measuring devices of the prior art typically employ some kind of contacting means for making a conductive connection with material in which moisture is to be measured so that the moisture can be determined by electrical conduction. Unfortunately, the contacting means or brushes are subject to breakage and shorting whereby the moisture indications tend to become inaccurate. Further, even if the brushes are in good condition, the degree of electrical contact provided with the material under test is nonuniform.

Moisture detectors have been developed which do not require contact with the material but instead employ capacitive coupling or the like. Many, however, are quite sensitive to the position of the material relative to the sensor conductor, as well as to the thickness of the material, and therefore indications derived on a production line basis can be somewhat undependable. Also, the conveying means upon which the material is transported can short out the measuring system such that a dependable reading is not obtained.

In prior U.S. Pat. No. 4,377,783, a measuring system is set forth in which transmitting and receiving plates are offset along the path of the measured material, and a conductive path in the veneer and the grounded conveyor is employed as part of the circuit. While very efficacious, there is again some dependency upon accurate contact with the material being measured.

In prior application Ser. No. 494,953 filed May 16, 1983 now U.S. Pat. No. 4,563,635 moisture in wood veneer strips is measured by passing the veneer strips between arrays of plates including a transmitting plate on one side of the veneer and a juxtaposed receiving plate on the other. Phase plates on either side of and on the same level as the transmitting plate are empowered by a signal having the reverse phase to that applied to the transmitting plate. When wet veneer passes between the plate arrays, part of the transmitted signal is shunted reducing the signal received by the receiving plate. While this approach reduces sensitivity to vertical position of the veneer strips, eliminates problems associated with accidental grounding of the veneer and eliminates the need for mechanical contact with the veneer, in practice some unwanted signal shunting occassionally occurs as a veneer sheet initially enters the space between the transmitting and receiving plates, resulting in a false moisture detection signal. Also, the moisture detection apparatus disclosed in the prior application requires use of electronics equipment both above and below the veneer. The equipment mounted below the veneer tends to collect dust and debris which can effect moisture readings.

It would therefore be desirable to provide a moisture detection apparatus wherein moisture detection is not only substantially independent of thickness variations in the veneer and of the vertical position of the veneer between detector and transmitter plates but is also independent of the horizontal position of the veneer as it approaches the transmitting and detecting plates. Further, it would be desirable if the detection apparatus were mountable largely in a single package above the veneer so that dust and debris cannot collect on lower portions of the apparatus and thereby interfere with moisture readings.

SUMMARY OF THE INVENTION

According to the present invention, in a preferred embodiment thereof, the material, e.g. wood veneer, is transported along a path into a region between a sensor assembly and a pair of sensor transmitter bars.

The sensor assembly comprises in part a detector plate, a pair of phase plates on either side of and on the same level as the detector plate, a signal plate parallel with and above the detector and phase signal plates, and a ground plate above and parallel with the signal plate. The sensor assembly also comprises a source of split phase oscillating signal having a neutral, designated "machine ground", coupled to the signal plate, a first oscillating signal output, designated "earth ground", coupled to the ground plate and to the sensor transmitter bars, and a second oscillating signal output, 180 degrees out of phase with the first oscillating signal output and coupled to the phase plates.

When there is no wet veneer between the sensor assembly and the transmitter bars, coupling between the sensor transmitter bars and the detector plate tends to drive the potential of the detector plate toward earth ground. At the same times coupling between the phase plates and the detector plate tends to drive the detector plate to a potential 180 degrees out of phase with earth ground, taking machine ground as a reference. As a result the detector plate, in the absence of a wet veneer, tends to float at a potential relatively near machine ground. When wet veneer enters the area between the sensor assembly and the transmitter bars, coupling increases between the detector plate and the earth grounded transmitter bars, driving the detector plate closer to earth ground. Thus the potential difference between the detector and signal plates is increased in the presence of wet veneer.

The sensor assembly further comprises a detector circuit, mounted above the ground plate, coupled to detect the potential difference between the detector and signal plates and to produce a control signal when the potential difference is high enough to indicate the presence of wet veneer. The control signal may then be used to drive a moisture indicator or alarm.

The ground plate shields equipment mounted above the ground plate from signals transmitted by the signal plate. The signal plate shields and the detector plate from the ground plate so that detector plate potential is primarily dependent on coupling between the detector plate and the phase plates and the transmitter bars. The phase plates help to compensate for changes in vertical position of the veneer; when the veneer moves higher, coupling between the detector plate and the transmitter bars increases driving the detector plate closer to earth ground. However, coupling between the phase plates and the detector plate also increases, driving the detector plate away from earth ground. The two effects tend to cancel for variations in vertical position of th veneer.

The present invention is thus insensitive to vertical position of the veneer and has demonstrated no false readings as veneer is inserted into the sensing area. Further, only the transmitter bars are located below the veneer presenting little opportunity for unacceptable collection of dust or debris. Also the transmitter bars, being at earth ground potential, may be connected to the signal source in the sensor assembly through structural steel only, eliminating the need for extensive wiring to interconnect circuits above and below the veneer.

It is accordingly an object of the present invention to provide an improved apparatus for detecting moisture in plywood veneer or other materials.

It is a further object of the present invention to provide an improved apparatus for moisture detection wherein such apparatus is economical in construction and reliable in operation.

It is another object of the present invention to provide an improved moisture detecting apparatus which is largely independent of vertical positioning of the material relative to the sensing means.

It is a further object of the present invention to provide an improved moisture detecting apparatus which is largely unaffected by collection of dust and debris on components mounted below the material.

It is a further object of the present invention to provide an improved moisture detecting apparatus which does not require extensive electrical connections between circuits above and below the material being tested.

The subject matter which we regard as out invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

DETAILED DESCRIPTION

Figure 4:
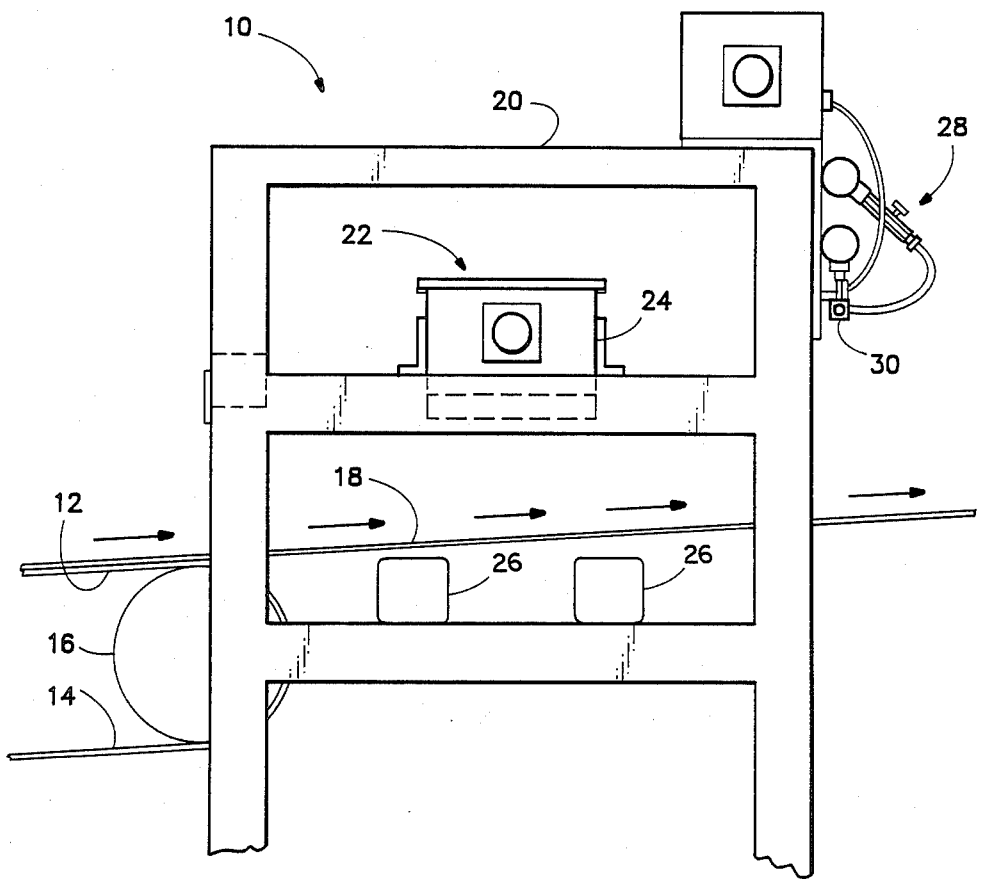
FIG. 4 is an end view of the moisture detecting apparatus of the present invention mounted in a frame.

Referring to the drawings and particularly to FIG. 4, illustrating moisture detecting apparatus 10 according to the present invention, a conveyor comprising upper run 12 and lower run 14, suitably comprising chains or belts, are trained about head roll 16. The conveyor receives a plurality of plywood veneer strips or pieces 18 from a veneer dryer (not shown), deposited upon the conveyor for transport in the direction indicated by the arrows between the legs of support table 20.

Table 20 carries therebeneath sensor assembly 22, contained in elongated cabinet 24, and transmitter bars 26 in parallel relation spaced about 4 inches apart underneath cabinet 24. The underside of cabinet 24 and the top of transmitter bars 26 are vertically spaced approximately four and one half inches apart in the specific example. Sensor assembly 22 and transmitter bars 26 extend perpendicular to the direction of motion of veneer strips 18 for the width of the conveyor. Table 20 also carries marking means 28 comprising sprayer 30 for marking veneer strips in which a predetermined amount of moisture is detected.

Figure 2:
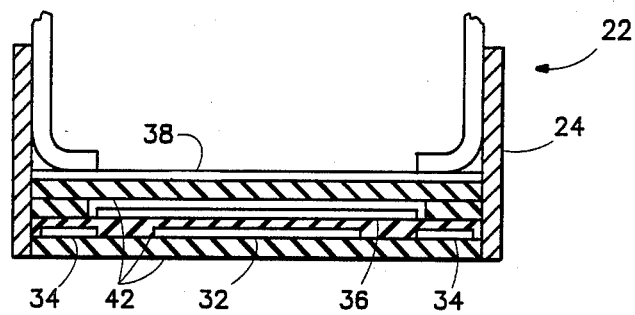
FIG. 2 is a cross-sectional view of a portion of the sensor assembly showing the relative placement of the phase signal plates, the detector plate, the signal plate and the ground plate according to the present invention.

Referring to FIG. 2, depicting a cross-sectional view of the lower portion of cabinet 24 of sensor assembly 22, contained in the underside of cabinet 24 are a plurality of longitudinally oriented conducting metal plates supported in generally facing relation to the veneer strips conveyed therebelow. Cabinet 24 centrally supports detector plate 32 and phase signal plates 34 disposed in laterally spaced relation on either side of detector plate 32 and in the plane thereof, i.e. such that a strip of veneer first passes under one of the phase signal plates 34, then under detector plate 32, and then under the other phase signal plate 34. In the specific example, detector plate 32 may have a width of approximately one and a half inches and a length comparable to that of cabinet 24 so as to extend along the width of the entire conveyor system. Phase signal plates 34 in the specific example are each about one half inch wide and are spaced approximately five inches from detector plate 32. Phase signal plates 34 are also comparable in length to the length of the entire cabinet.

Signal plate 36 is also centrally mounted on the underside of cabinet 24 approximately one sixteenth inch above and in parallel relation with detector plate 32, the plates being seperated by insulating material 42. Signal plate 36, in the specific example, is approximately four and a half inches wide, extending about one and a quarter inch beyond either edge of detector plate 32. Ground plate 38 is mounted on top of the under side of cabinet 24 about one quarter inch above and in parallel relation with signal plate 36, separated by insulating material 42. Ground plate 38 extends over the width of the underside of cabinet 24, approximately twenty inches in the specific example. Ground plate 38 and signal plate 36 are also comparable in length to the length of cabinet 24.

The arrays of plates suitably comprise printed or etched conductors on circuit board sections, insulators 42, composed of epoxy glass and forming the bottom of cabinet 24.

Figure 3:
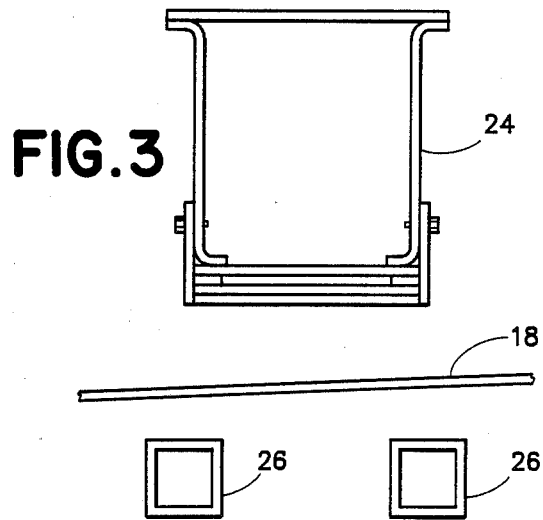
FIG. 3 is a cross-sectional view of the present invention showing the relative position of the sensor assembly, the sensor transmitter bars, and the material being tested.

Referring to FIG. 3, depicting a cross-sectional view of cabinet 24 and sensor transmitter bars 26 and veneer strip 18, the top runs 12 of the conveyor are positioned so that the strips 18 of veneer will pass between cabinet 24 and transmitter bars 26 about one half to one inch above the transmitter bars. This spacing is suitable for measuring moisture in wood having a thickness from a fraction of an inch up to about two inches. The strips 18 of veneer may travel at a small angle from horizontal without effecting operation of the present invention.

Figure 1:
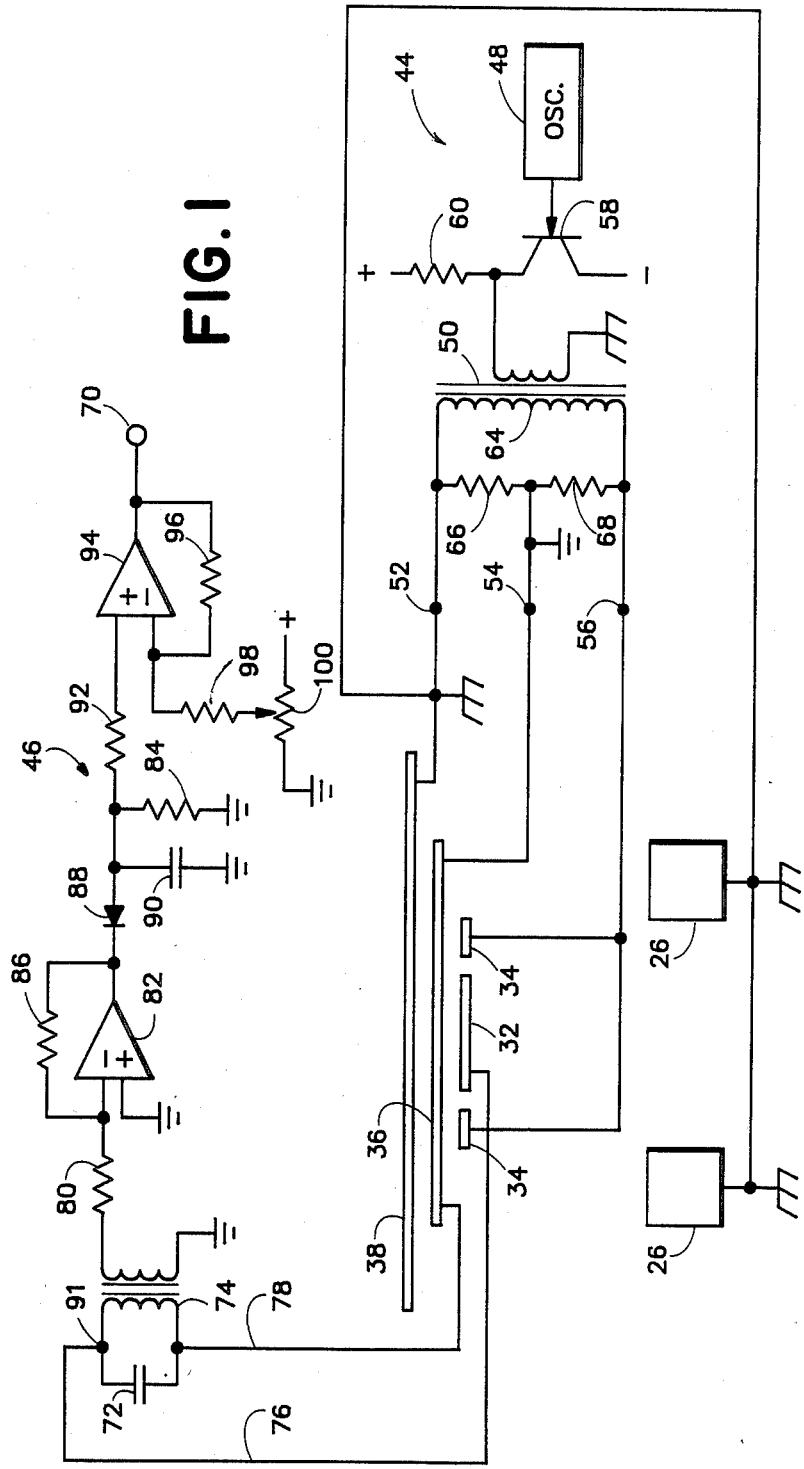
FIG. 1 is a combination schematic and block diagram of the moisture detecting apparatus according to the present invention.

Referring to FIG. 1, a combination circuit and block diagram is illustrated for the moisture detector 10 according to the present invention. In addition to plates 32, 34, 36 and 38 mounted on the underside of cabinet 24 sensor assembly 22 further comprises signal generating means 44. Signal generating means 44 produces radio frequency (suitably 100 KHz) signals at terminals 52 and 56. With terminal 54 taken as a neutral reference, "machine ground", the signals at terminals 52 and 56 are 180 degrees out of phase with one another. Signal generating means 44 comprises oscillator 48, suitably comprising a type 12060 integrated circuit manufactured by Motorola, with output to a gate terminal of a VMOS field effect transistor 58. Transistor 58, suitably comprising a type VN10KM, has a source terminal connected to a negative supply and a drain terminal connected to a positive supply via resistor 60. Signal generating means 44 further comprises Ferroxcube cored transformer 50, with primary driven by the drain voltage of transistor 58, having secondary winding 64 shunted by resistors 66 and 68 in series. The junction of resistors 66 and 68 forms machine ground terminal 54 while the two leads of the transformer 50 secondary winding provide the earth ground signal at terminal 52 and the reverse phase signal at terminal 56.

Detector means 46, connected to detector plate 32 via lead 76 and to signal plate 36 via lead 78, includes a tuned circuit comprising parallel connected capacitor 72 and the primary winding of ferrite core transformer 74 tuned substantially to the frequency of signal generating means 44. The signal across the tuned circuit is coupled through transformer 74 and input resistor 80 to a first operational amplifier 82 provided with a feedback resistor 86 and a second input terminal grounded. The AC output of amplifier 82 is detected with diode 88 having its anode coupled to an input of comparator amplifier 94 through resistor 92 and shunted to ground through capacitor 90 in parallel with resistor 84. Amplifier 94 is provided with a second input terminal coupled via resistor 98 to the moveable tap of potentiometer 100 connected between a positive voltage and ground. The potential between detector plate 32 and signal plate 36 is amplified by amplifier 82 and detected by diode 88 to provide a negative voltage across capacitor 90. A second input of comparator amplifier 94 is set by means of potentiometer 100 to establish a threshold such that if the negative charge on capacitor 90 increases above a predetermined level, the output at terminal 70 will, via intermediate amplifiers not shown, operate sprayer 30. That is, moisture is ordinarily indicated when the negative voltage on capacitor 90 is relatively high. Feedback resistor 96 produces a hysteresis effect such that once the sprayer starts to operate, it will continue to do so until the negative voltage across capacitor 90 decreases to a negative value less than the value at which spraying started, whereby eratic or intermittent operation of sprayer 30 is prevented.

Signal plate 36 is coupled to terminal 54 and is thus held at machine ground. Ground plate 38 and sensor transmitter bars 26 are coupled to earth ground at terminal 52. Phase signal plates 34 are coupled to terminal 56 such that the potential on phase signal plates 34 is 180 degrees out of phase with earth ground.

Considering the overall operation of the moisture detecting apparatus 10 illustrated in FIGS. 1 through 4, when there is no wet veneer 18 between sensor assembly 22 and transmitter bars 26, coupling between sensor transmitter bars, at earth ground, and detector plate 32 tends to drive detector plate 32 toward earth ground. At the same time coupling between phase plates 34 and detector plate 32 tends to drive the detector plate to a potential 180 degrees out of phase with earth ground. As a result detector plate 32 in the absence of wet veneer 18, tends to float at a potential relatively near machine ground. Therefore the potential difference between detector plate 32 and signal plate 36 is relatively small in the absence of wet veneer.

When wet veneer 18 enters the area between sensor assembly 22 and transmitter bars 26, coupling between transmitter bars 26, at earth ground, and detector plate 32 increases, driving the detector plate closer to earth ground. Thus the potential difference between detector plate 32 and signal plate 36, at machine ground, is relatively larger in the presence of wet veneer 18, and generally increases with the dampness of the veneer.

The increase in potential difference between detector plate 32 and signal plate 36 caused by insertion of wet veneer 18 between sensor assembly 22 and sensor transmitter bars 26 results in an increase in negative charge across capacitor 90 in detector means 46. If the negative voltage across capacitor 90 is larger than the positive voltage applied to the inverting input of comparator amplifier 94, comparator amplifier 94 initiates a control signal at terminal 70 causing sprayer 30 to mark the wet veneer. Potentiometer 100 is set such that a control signal output at terminal 70 does not occur unless the negative voltage across capacitor 90 is sufficiently large. Since the voltage across capacitor 90 increases negatively with the dampness of veneer 18, sprayer 30 does not operate unless veneer 18 is sufficiently damp. Thus the minimum dampness necessary to initiate spraying may be controlled by adjustment of potentiometer 100.

As the thickness of veneer 18 increases, or as the height of the veneer above the sensor transmitter bars increases, coupling between the veneer and the detector plate increases, tending to drive the potential of detector plate 32 closer to earth ground. However, at the same time, coupling between phase signal plates 34 and detector plate 32 also increases tending to drive the potential of detector plate 32 180 degrees out of phase from earth ground. Thus the change in signal coupling from phase plates 34 tends to offset the change in the signal coupling from the veneer due to variations in the thickness or vertical position of the veneer, reducing the possibility of a false indication of wetness.

Since the signal detected by sensor assembly 22 is not dependent on signal shunting by veneer 18 partial insertion of veneer 18 in the sensing area beneath sensor assembly 22 does not result in false moisture readings. Also, since dry veneer is of low conductivity, and since detection of moisture depends on the coupling of a large portion of the veneer in the sensor area to earth ground, inadvertent or intentional grounding of the veneer outside the sensing area has no significant affect on moisture sensitivity.

As can be seen, most of the sensing apparatus is contained within cabinet 24 mounted above the veneer. Only the two sensor transmitter bars 26 are mounted below the veneer. Since these bars are connected to earth ground, they may be coupled to equipment in cabinet 24 through the structural steel of table 20. Therefore no wiring is required between sensing equipment mounted above and below the veneer. Also sensor transmitter bars 26 have small upper surface areas which do not collect much dust or debris and are relatively simple to clean in any case.

While the detection of moisture in veneer is particularly set forth herein, it will be understood that the apparatus is not restricted thereto but is applicable to other materials.

While we have shown and described a preferred embodiment of our invention, it will be apparent to those skilled in the art that many changes and modifications may be made without departing from our invention in its broader aspects. We therefore intend the appended claims to cover all such changes and modifications as fall within the true spirit and scope of our invention.

We claim:

1. Apparatus for measuring the moisture content of material, said apparatus comprising:
- first conductor means disposed in spaced facing relation to said material;
- second conductor means disposed in spaced facing relation to said material and in adjacent spaced relation to said first conductor means;
- third conductor means disposed in facing relation to said material and positioned opposite said first and second conductor means while being generally separated from said first and second conductor means by said material during the presence of said material;
- receiving means;
- means for energizing said first and third conductor means in out of phase relation with respect to a common reference whereby coupling between first and second conductor means and coupling between second and third conductor means create a potential in said second conductor means during the presence or absence of said material; and
- means for connecting said second conductor means to said receiving means for registering said potential of said second conductor means with respect to a fixed reference potential whereby moisture in said material is disposed in coupling relation between said second and third conductor means to alter the potential of said second conductor means so that moisture can be detected according to the change in potential of said second conductor means.

2. The method of measuring the moisture content of material comprising:
- passing a first radio frequency signal through said material for reception by a receiving plate;
- transmitting a second radio frequency signal in out-of-phase relation to said first radio frequency signal with respect to a common reference, said second signal being transmitted from a source adjacent said receiving plate without passing through said material, said first and second radio frequency signals inducing a potential in said receiving plate, the induction of said first radio frequency signal varying in accordance with the moisture contained in said material; and
- measuring the potential of said receiving plate to determine the extent of said moisture.

3. The apparatus according to claim 1 wherein said third conductor means comprises at least one grounded conductive bar positioned beneath the path of said material, said first and second conductor means being located above the path of said material such that said material passes between said third conductor means and the other conductor means.

4. Apparatus for measuring the moisture content of material being conveyed on a conveyor along a generally horizontal path, said apparatus comprising:
- a detector conductor adjacent the path of said material on a first side of said conveyor so as to face a first side of said material conveyed on said conveyor;
- a first transmitting conductor positioned generally opposite said detector conductor in sufficiently close proximity to said detector conductor so that radio frequency energy can be coupled between said first transmitting conductor and said detector conductor, said first transmitting conductor being adjacent the path of said material on a second side of said conveyor so as to face a second side of material as conveyed on said conveyor;
- an additional transmitting conductor positioned adjacent said detector conductor on said first side of said conveyor in sufficiently close proximity to said detector conductor so that radio frequency energy can also be coupled between said additional transmitting conductor and said detector conductor;
- receiving means;
- means for providing a source of radio frequency energy connected between said first transmitting conductor and said additional transmitting conductor for energizing said first and additional conductors in opposite phase relation with respect to one another whereby coupling between said transmitting conductors and said detector conductor creates a potential in said detector conductor; and
- means for connecting said detector conductor to said receiving means for registering said potential of said detector conductor whereby when moisture in said material is disposed in coupling relation between said first transmitting conductor and said detector conductor, the potential of said detector conductor is altered so that moisture can be detected according to the change in potential of said detector conductor.

5. The apparatus according to claim 4 wherein said first transmitting conductor comprises at least one grounded bar positioned beneath the path of said material.

6. The apparatus according to claim 4 wherein said first transmitting conductor comprises a pair of grounded bars positioned beneath the path of said material, and wherein said additional transmitting conductor comprises a pair of plates positioned above the path of said material.

7. The apparatus according to claim 6 wherein said detector conductor is positioned between said pair of plates.

8. Apparatus for measuring the moisture content of material being conveyed on a conveyor along a generally horizontal path, said apparatus comprising:
- a detector conductor adjacent the path of said material on a first side of said conveyor so as to face a first side of said material conveyed on said conveyor;
- a first transmitting conductor positioned generally opposite said detector conductor in sufficiently close proximity to said detector conductor so that radio frequency energy can be coupled between said first transmitting conductor and said detector conductor, said first transmitting conductor being adjacent the path of said material on a second side of said conveyor so as to face a second side of material as conveyed on said conveyor;
- an additional transmitting conductor positioned adjacent said detector conductor on said first side of said conveyor in sufficiently close proximity to said detector conductor so that radio frequency energy can also be coupled between said additional transmitting conductor and said detector conductor;
- receiving means;
- means for providing a source of radio frequency energy connected between said first transmitting conductor and said additional transmitting conductor whereby coupling between said transmitting conductors and said detector conductor creates a potential in said detector conductor;

wherein said means for providing a source of radio frequency energy includes first and second output terminals coupled respectively to said first and additional transmitting conductors;

means for connecting said detector conductor to said receiving means for registering said potential of said detector conductor whereby when moisture in said material is disposed in coupling relation between said first transmitting conductor and said detector conductor, the potential of said detector conductor is altered so that moisture can be detected according to the change in potential of said detector conductor;

wherein said means for connecting said detector conductor to said receiving means includes a return path at a reference level intermediate said first and second terminals of said source of high frequency energy;

a signal plate connected to said return path and positioned on the remote side of said detector conductor from said first transmitting conductor; and a grounding plate located on the remote side of said signal plate from said first transmitting conductor.

9. The apparatus according to claim 4 wherein said means for providing a source of radio frequency energy includes first and second output terminals coupled respectively to said first and additional transmitting conductors, and wherein said means for connecting said detector conductor to said receiving means includes a return path at a reference level intermediate said first and second terminals of said source of high frequency energy.

10. The apparatus according to claim 9 further including a signal plate connected to said return path and positioned on the remote side of said detector conductor from said first transmitting conductor.

11. Apparatus for measuring the moisture content of material being conveyed on a conveyor along a generally horizontal path, said apparatus comprising:

a detector conductor adjacent the path of said material on a first side of said conveyor so as to face a first side of said material conveyed on said conveyor;

a first transmitting conductor positioned generally opposite said detector conductor in sufficiently close proximity to said detector conductor so that radio frequency energy can be coupled between said first transmitting conductor and said detector conductor, said first transmitting conductor being adjacent the path of said material on a second side of said conveyor so as to face a second side of material as conveyed on said conveyor, wherein said first transmitting conductor comprises a pair of grounded bars positioned beneath the path of said material;

an additional transmitting conductor positioned adjacent said detector conductor on said first side of said conveyor in sufficiently close proximity to said detector conductor so that radio frequency energy can be coupled between said additional transmitting conductor and said detector conductor, wherein said additional transmitting conductor comprises a pair of plates positioned above the path of said material and wherein said detector conductor is positioned between said pair of plates;

receiving means;

means for providing a source of radio frequency energy connected between said first transmitting conductor and said additional transmitting conductor whereby coupling between said transmitting conductors and said detector conductor creates a potential in said detector conductor;

means for connecting said detector conductor to said receiving means for registering said potential of said detector conductor whereby when moisture in said material is disposed in coupling relation between said first transmitting conductor and said detector conductor, the potential of said detector conductor is altered so that moisture can be detected according to the change in potential of said detector conductor; and further including a grounding plate located above said detector conductor on the remote side of said detector conductor from said first transmitting conductor.

* * * * *